(12) United States Patent
Amary et al.

(10) Patent No.: US 7,184,145 B2
(45) Date of Patent: Feb. 27, 2007

(54) ACHROMATIC SPECTROSCOPIC ELLIPSOMETER WITH HIGH SPATIAL RESOLUTION

(75) Inventors: Pascal Amary, Saint Pryve Saint Mesmin (FR); Ramdane Benferhat, Oncy sur Ecole (FR); Francis Bos, Longjumeau (FR); Denis Cattelan, Paris (FR)

(73) Assignee: Horiba Jobin Yvon, Inc., Longjumeau (FR)

( * ) Notice: Subject to any disclaimer, the term of this patent is extended or adjusted under 35 U.S.C. 154(b) by 145 days.

(21) Appl. No.: 10/518,121

(22) PCT Filed: Jun. 16, 2003

(86) PCT No.: PCT/EP03/06316

§ 371 (c)(1),
(2), (4) Date: Dec. 15, 2004

(87) PCT Pub. No.: WO03/106979

PCT Pub. Date: Dec. 24, 2003

(65) Prior Publication Data

US 2006/0164642 A1   Jul. 27, 2006

(30) Foreign Application Priority Data

Jun. 17, 2002 (EP) ................... 02291510

(51) Int. Cl.
*G01J 4/00* (2006.01)
(52) U.S. Cl. .................................. 356/369
(58) Field of Classification Search ............... None
See application file for complete search history.

(56) References Cited

U.S. PATENT DOCUMENTS

| 4,210,401 | A | 7/1980 | Batten |
| 5,910,842 | A | 6/1999 | Piwonka-Corle et al. |
| 6,804,003 | B1 * | 10/2004 | Wang et al. ................ 356/369 |
| 6,804,004 | B1 * | 10/2004 | Johs et al. ................. 356/369 |
| 2002/0191185 | A1 * | 12/2002 | Rotter et al. ............... 356/369 |

OTHER PUBLICATIONS

PCT/EP03/06316 International Search Report.
XP000237482 2219 Applied Optics 30 Nov. 1, 1991. No. 31 New York, US, pp. 4471-4473.

* cited by examiner

*Primary Examiner*—Tu T. Nguyen
(74) *Attorney, Agent, or Firm*—Anthony H. Handal, Esq.; Brown Rudnick Berlack Israels LLP

(57) ABSTRACT

Disclosed is an achromatic spectroscopic ellipsometer for analyzing small regions of a sample over a wide range of wavelengths from ultraviolet (UV) to infrared (IR). The spectroscopic ellipsometer contains a light source emitting a light beam which passes through a polarisation state generator section before being focused at an incidence angle q by a first parabolic mirror to a small spot on a sample. A second parabolic mirror collects the reflected beam and connects said beam to an analyzing section. The reflected beam emerges from the analyzing section and is spectroscopically detected and analyzed. The light beam through the polarisation state generator section up to the first parabolic mirror and the light beam from the second mirror through the analyzing section are parallel enabling achromatism. The incidence angle q is largely varied without shifting of the location of the small spot on the sample surface.

15 Claims, 5 Drawing Sheets

ACHROMATIC SPECTROSCOPIC ELLIPSOMETER WITH HIGH SPATIAL RESOLUTION

CROSS-REFERENCE TO RELATED APPLICATIONS

This is a National Stage application of PCT/EP03/06316, filed Jun. 16, 2003 which claims benefit of European Patent Application 02291510.2, filed Jun. 17, 2002.

BACKGROUND OF THE INVENTION

The invention relates to ellipsometric systems with an achromatic design for analysing small area of a sample over a wide of wavelengths from ultraviolet (UV) to infrared (IR).

Spectroscopic ellipsometry is a well-known non destructive probe to analyse the properties of a sample (or a layer over a sample). The surface of the sample is illuminated by a luminous beam that is reflected and the polarisation state of the reflected beam (that may be transmitted) is compared to that of the incident beam. This technique allows determining different properties of said sample. These properties may be, for example, the thickness and optical properties of different coatings (single layer or multiple layers) deposited on any substrate.

In conventional ellipsometry, the polarisation vector E of a beam is generally represented by its projections Es and Ep, respectively perpendicular and parallel to the incidence plane. The ratio denoting the change in the polarisation state produced by the interaction of a beam with a surface studied is generally represented by the complex quantity:

$$\rho = tg\Psi \exp(i\Delta) = (Ep/Es)^r/(Ep/Es)^i$$

The aim therefore is to measure the independent parameters $\Psi$ and $\Delta$ for a given surface.

A description of ellipsometry and ellipsometer systems can be found in the book of AZZAM and BASHARA entitled "Ellipsometry and Polarised Light", North-Holland, Amsterdam, 1977. Different types of spectroscopic ellipsometers exist in the industry: rotating analyser (ASPNES D. E. et al; Appl. Opt. (1975) 200), rotating polariser, rotating compensator and phase modulated ellipsometer (BOYER G. R. et al. Appl. Opt. 18 (1979) 217).

Due to the high integration in microelectronics and the new developed materials, high sensitivity measurements of optical properties are required.

It is thus highly desirable to obtain a small and compact spot of the focused beam on the sample surface and to have a large range of incidence angle so that the ellipsometer has a high degree of sensitivity for film variations on various substrates. The focused beam on the surface should however show no aberrations in order to fit the microscopic structures.

The current state, of the art ellipsometers employ reflective optics to avoid geometric aberrations and to obtain a continuous incident angular range.

In "Angular scanning mechanism for ellipsometers", BYRNE D. M. and MAC FARLANE D. L.; Appl. Optics, 30 (1991) 4471, an ellipsometer was proposed in which a pair of stationary concave ellipsoidal mirrors had respectively at their near focus a rotating flat mirror and at their coincident far focus, a sample. By rotating the flat mirror, it was demonstrated a continuously varying angle of incidence on the sample while maintaining a fixed point of incidence. A large range of incidence angle could be achieved with a control on said angle variation only depending on the characteristics of the ellipsoid.

However, since the beam was incident on the mirrors with an angle different from zero, the reflection of said beam introduced a change in the polarisation. These modifications had to be measured and taken into account in the data analysis.

More recently, PIWONKA-CORLE et al. [U.S. Pat. No. 5,910,842] have demonstrated the use of mirrors with elliptical shape surfaces to reduce off-axis aberrations such as <<coma>> in the focused beam.

The described system showed however chromatic aberrations. These aberrations could only be minimised by employing Rochon prisms for the first polariser and the analyser, whose length along the axis of propagation of the light beam was minimised.

The incidence angle range was limited to angles superior to 60° from the normal to the surface to limit the modifications in the beam polarisation upon reflection on the mirrors.

Although, PIWONKA-CORLE et al. tried to minimise them, both previously described systems showed chromatic aberrations.

BRIEF SUMMARY OF THE INVENTION

The purpose of the invention is to remedy the short comings mentioned above and to propose a system having one or more of the following features and advantages: namely, an achromatic design, a large range of incidence angle, a small spot of the focused beam on the sample surface, a simple and compact design, a straightforward use and a fast data acquisition.

To this end, the invention concerns a spectroscopic ellipsometer, comprising:
  a light source emitting a light beam,
  a polarisation state generator section containing a collimation optic collimating said beam and a generator of polarisation that polarises the beam,
  a first mirror focusing the beam to a small spot on the surface of a sample at an incidence angle θ,
  a second mirror connecting the beam modified by the sample to an analysing section comprising a polarisation analyser that analyses the beam,
  means for detecting and analysing spectroscopically said beam.

According to the invention,
  the first and second mirrors are parabolic mirrors,
  the light beam through the polarisation state generator section up to the first mirror is parallel enabling achromatism,
  the light beam from the second mirror through the analysing section is parallel enabling achromatism,
  said incidence angle θ is largely varied without shifting of the location of the small spot on the sample surface.

We mean by <<largely varied>>, the value of the incidence angle θ can be changed from 0 to 90 degrees. We also mean by "the beam modified by the sample", the transmission or reflection of the beam by the sample that changes its polarisation state.

According to various embodiments, the present invention also concerns the characteristics below, considered individually or in all their technical possible combinations:
  the generator of polarisation is a photoelastic modulator,
  the generator of polarisation is a rotating analyser,
  the generator of polarisation is a rotating polariser,
  the generator of polarisation is a rotating compensator, the polarisation state generator section and the analysing section are translated vertically with respect to the parabolic mirrors to vary the incidence angle θ, both mirrors and the sample are vertically translated with respect to the analysing section and polarisation state generator section to vary the incidence angle θ, the incidence angle θ is varied between 0° and 90°, the said two parabolic mirrors have the same optical characteristics, the axis of both parabolic mirrors and the sample surface are merged, both parabolic mirrors are positioned symmetrically with respect to a plane passing by their optical axis and being normal to the sample surface, the shape of the parabolic mirrors is manufactured by diamond turning, the distance from the polarisation state generator section to the sample, and the distance from the analysing section to the sample are optimised to avoid diffraction influence created by diamond turning artefact, the parabolic mirrors are treated with a post-polishing process, the size of the spot is close to the diffraction limits.

BRIEF DESCRIPTION OF DRAWINGS

To facilitate further description of the invention, the following drawings are provided in which.

These drawings are provided for illustrative purposes only and should not be used to unduly limit the scope of the invention.

DETAILED DESCRIPTION OF THE INVENTION

Ellipsometry is a powerful probe to obtain optical measurements on thin films. The optical reflectivity of a thin film (single or multilayers) is determined by measuring the change in the polarisation state of a light beam upon reflection on said thin film. The purpose of the present invention is to disclose a spectroscopic ellipsometric system having a wide spectral bandwidth from ultraviolet (UV) to infrared (IR), an achromatic focused beam and a large range of incidence angles. We shall call hereinafter the <<incidence angle>>, the angle at which the focused beam strikes the sample surface with respect to the normal to the surface. For example, a beam with normal incidence at the sample surface has an incidence angle of zero degree.

We shall call as well a <<small spot>>, a compact spot on sample with preferably a square-shape, said spot being obtained by projection onto the sample surface of a beam whose transversal dimensions prior to said projection are typically inferior to 25 μm×25 μm.

Figure 1:
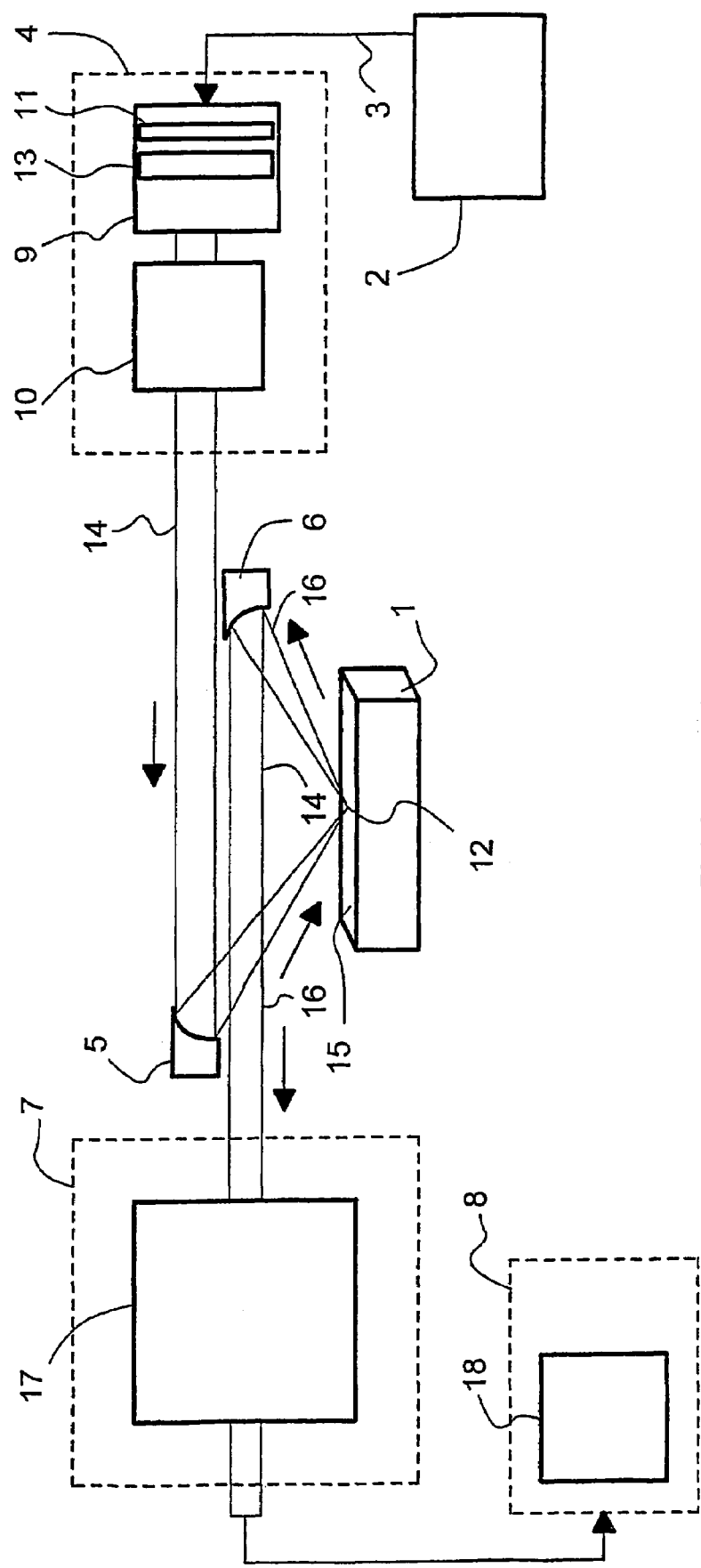
FIG. 1 is a schematic view of a first embodiment of the invention.

Hereinafter preferred embodiments of the invention will be described with reference to the appended drawings. FIG. 1 shows a first embodiment of the ellipsometric system.

The ellipsometric system aims to measure a sample 1. Said system comprises a light source 2 emitting a light beam 3. This beam 3 shows in a first embodiment a continuous spectrum of wavelengths ranging typically from the ultraviolet (UV) to the infrared (IR) regions of the electromagnetic radiation spectrum. In a second embodiment, the beam contains a flux centred on a single wavelength λ.

The system also comprises a polarisation state generator section 4, a first 5 and a second 6 parabolic mirrors, an analysing section 7 and means 8 for detecting and spectroscopically analysing said beam.

The light beam 3 emitted by the light source 2 goes first through the polarisation state generator section 4. Said section contains a collimation optic 9 collimating the light beam 3 and a generator of polarisation 10 that polarises said beam 3. The collimation optic 9 comprises a pinhole 11 placed at the focus of the collimation optic 9 to control the desired size of the spot 12 on the sample 1, and a diaphragm 13 to control the aperture of the beam 3.

The generator of polarisation 10 polarises the beam 3 propagating through it, and the polarisation state of the polarised beam 14 emerging from it is hence precisely known.

Polarised beam 14 emerges from the polarisation state generator section 4 to fall on the first parabolic mirror 5. Through the polarisation state generator section 4 up to the first parabolic mirror 5, the polarised beam 14 is a parallel beam. Advantageously, the beam 14 is therefore achromatic.

Polarised beam 14 is then reflectively focused by the first parabolic mirror 5 on the surface 15 of the sample 1.

In a preferred embodiment, the axis of the mirror 5 is merged with the sample surface 15 and the sample is therefore positioned at the focus of the mirror 5.

Advantageously, both parabolic mirrors 5, 6 are manufactured by diamond turning. Since diamond turning may create some grooves on the surface of the parabolic mirrors 5, 6 a post-polishing process is used. This process consists firstly in a nickel (Ni) layer (of 1000 Å) deposit followed by a polishing step in order to minimise the grooves on the mirrors. Finally, a copper (Cu) or an aluminum (Al) layer (of 1000 Å) is deposited on top.

The second parabolic mirror 6 receives the light beam 16 reflected from the sample 1. In a preferred embodiment, the first 5 and second 6 parabolic mirrors are rotated and positioned such as to obtain a symmetrical system with respect to a plane passing by their common respective axis, said plane being normal to the sample surface. Both mirrors 5, 6 have in this embodiment the same optical characteristics. In a particular implementation, the focal length is f=50.8 mm and the diameter=25.4 mm.

Advantageously, their axis are merged with the sample surface 15.

In a preferred embodiment, the distance from the polarisation section generator 4 to the sample 1, and the distance from the analysing section 7 to the sample 1 are optimised to avoid diffraction influence created by diamond turning artefact.

In a particular embodiment, spatial filters are placed on the path of the beam 14, 16 before and after reflection on the sample 1. These filters reduce possible side effects resulting from the presence of grooves on the surface of the parabolic mirrors 5, 6. After collection by the second parabolic mirror 6, the reflected light beam 16 goes in a parallel beam through the analysing section 7.

The analysing section 7 contains a polarisation analyser 17 to analyse the change in the polarisation state of the polarised beam 14 upon reflection at sample 1.

The generator of polarisation 10 of the embodiment described up to here is for example a rotating polariser, i.e. a polariser that rotates about the optical axis while the polarisation analyser 17 remains fixed. Alternatively, a photoelastic modulator can be used in place of the rotating polariser. In another embodiment, the analyser 17 may rotate during measurement of a sample while the polariser is fixed. The generator of polarisation 10 is hence a rotating analyser. Other particular embodiments employ as a generator of polarisation 10, a rotating compensator.

To obtain additional information about a given film or to measure a complicated film stack, it is necessary to perform measurements with various initial settings. The variable parameter may then be the wavelength at which the measurement is performed or the incidence angle θ.

In a particular implementation, the incidence angle θ is fixed and the light beam has a continuous spectrum of wavelengths. The reflected beam 16 emerging from the analysis section 7 goes to means 8 for detecting and spectroscopically analysing said beam. In a preferred embodiment, these means 8 contains a detector 18 that is able to acquire simultaneously several wavelengths.

Figure 2:
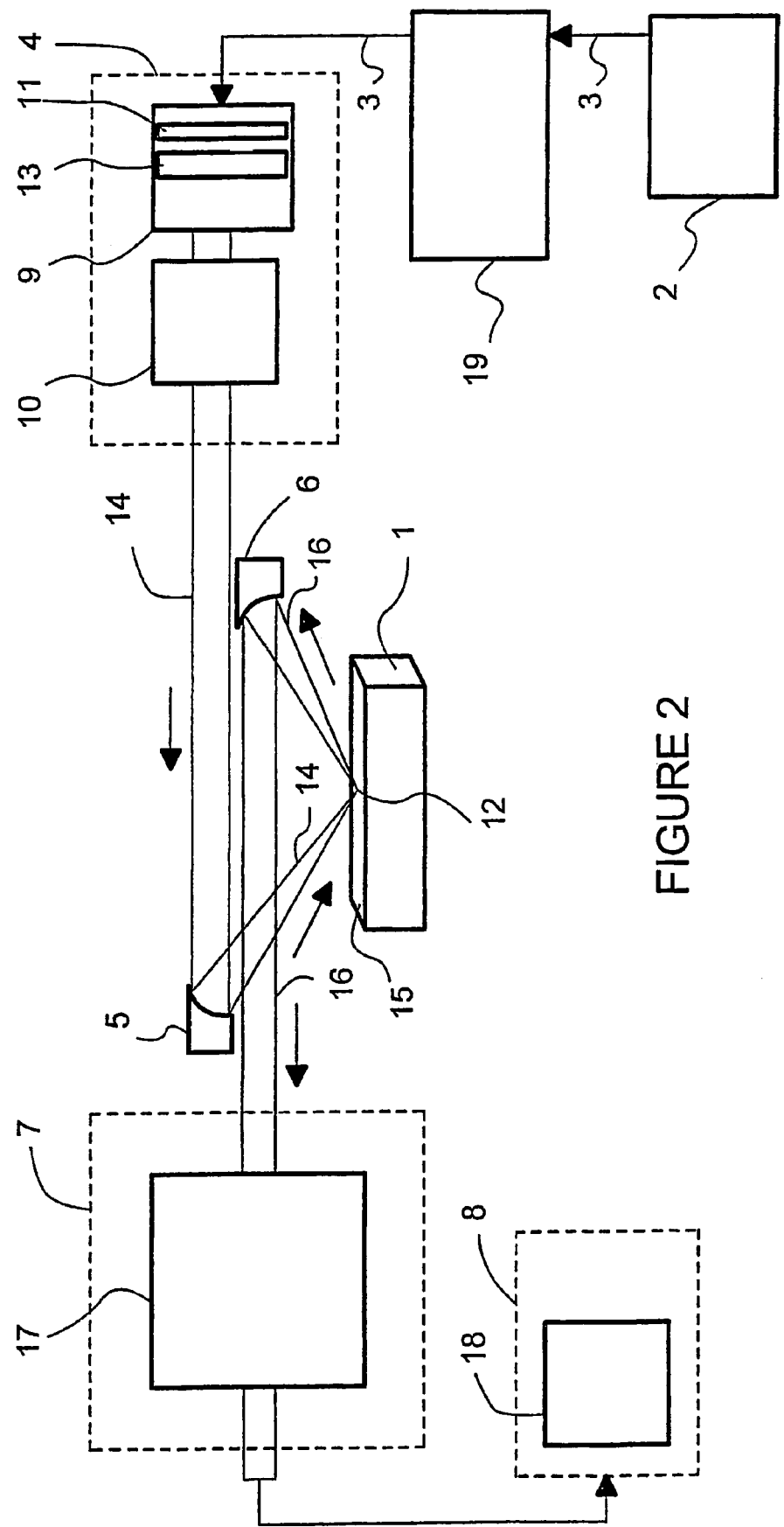
FIG. 2 is a schematic view of a second embodiment of the invention.

FIG. 2 shows a second embodiment of the present invention. This embodiment is the same as the first embodiment, but is different from the first embodiment in that it contains a monochromator 19. In FIG. 2, the same marks as those of FIG. 1 show the same things. That is to say, a monochromator 19 is provided on the light path connecting the light source 2 and the polarisation state generator section 4. The monochromator 19 selects a single wavelength among the continuous spectrum of the light beam 3 emitted by the broadband light source 2. The selection is particularly useful to study a continuous spectrum or a particular wavelength.

Figure 3:
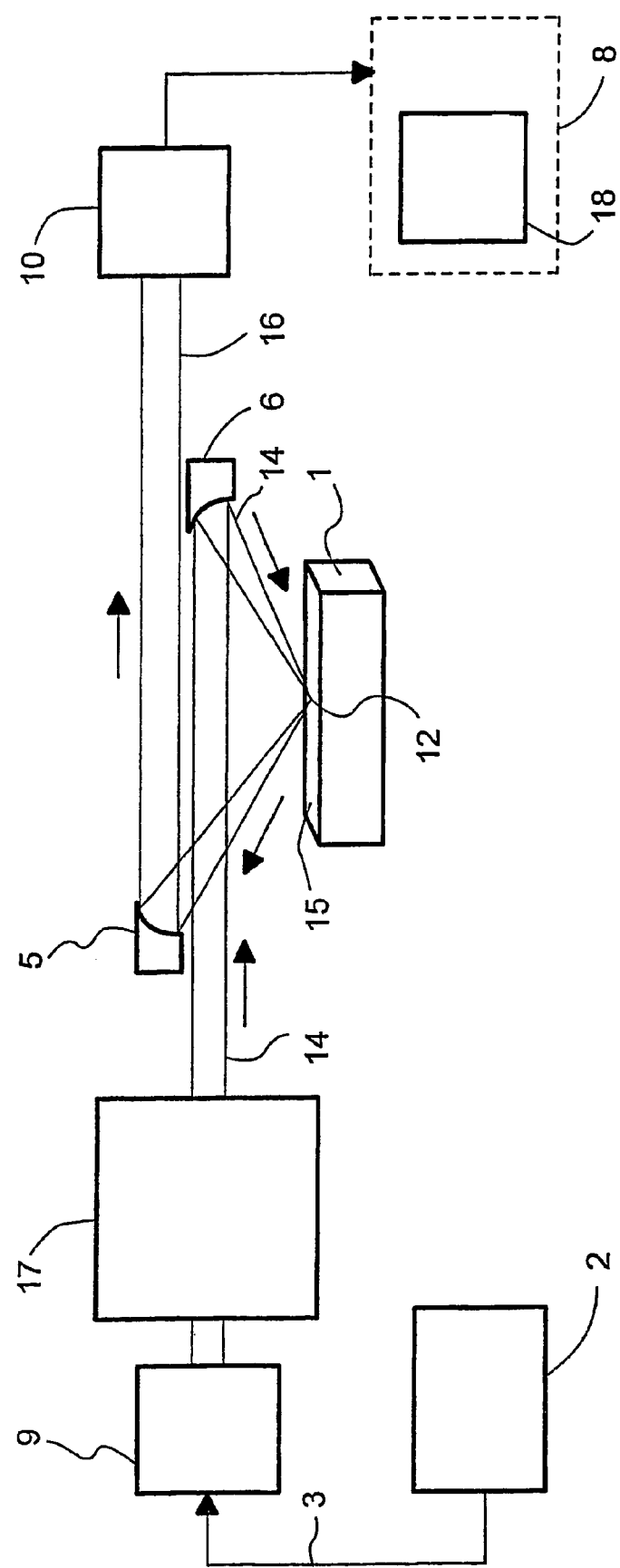
FIG. 3 is a schematic view of a third embodiment of the invention.

FIG. 3 shows a this embodiment of the present invention. The same marks in FIG. 3 as those in FIG. 1 show the same things.

In this respect, this embodiment makes no difference from the first embodiment in the respective constitutions of the ellipsometric system from the polarisation analyser 17 to the generator of polarisation 10, but is different from the first embodiment in the points of arranging the light source 2, the collimation optic 9 and the means 8 for detecting and analysing spectroscopically the light beam. That is to say, the light source 2 emits a light beam 3 which goes to the collimation optic 9. Said beam 3 emerges from the collimation optic 9 to go through the polarisation analyser 17. The means 8 for detecting and analysing the reflected beam 16 from sample 1 are placed after the generator of polarisation 10. For all the embodiments described up to now in FIG. 1 to 3, it is desirable to vary the incidence angle θ at fixed wavelength measurements.

Figure 4:
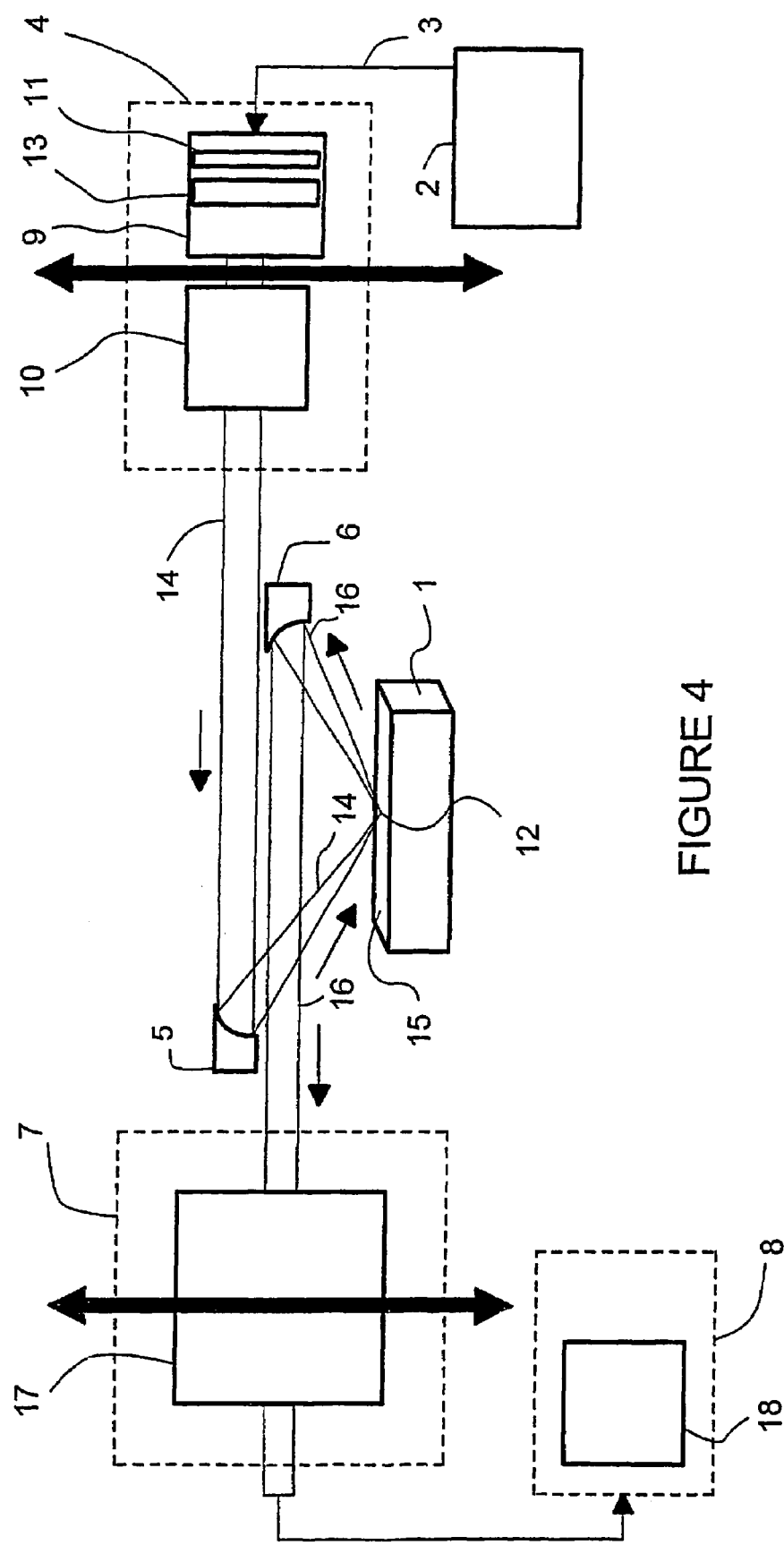
FIG. 4 shows the relative movement of the polarisation state generator section and analysing section with respect to both parabolic mirrors to vary the incidence angle θ.

FIG. 4 shows a first embodiment, in which the polarisation state generator section 4 and the analysing section 7 are translated vertically with respect to the parabolic mirrors 5, 6 to vary the incidence angle θ.

Figure 5:
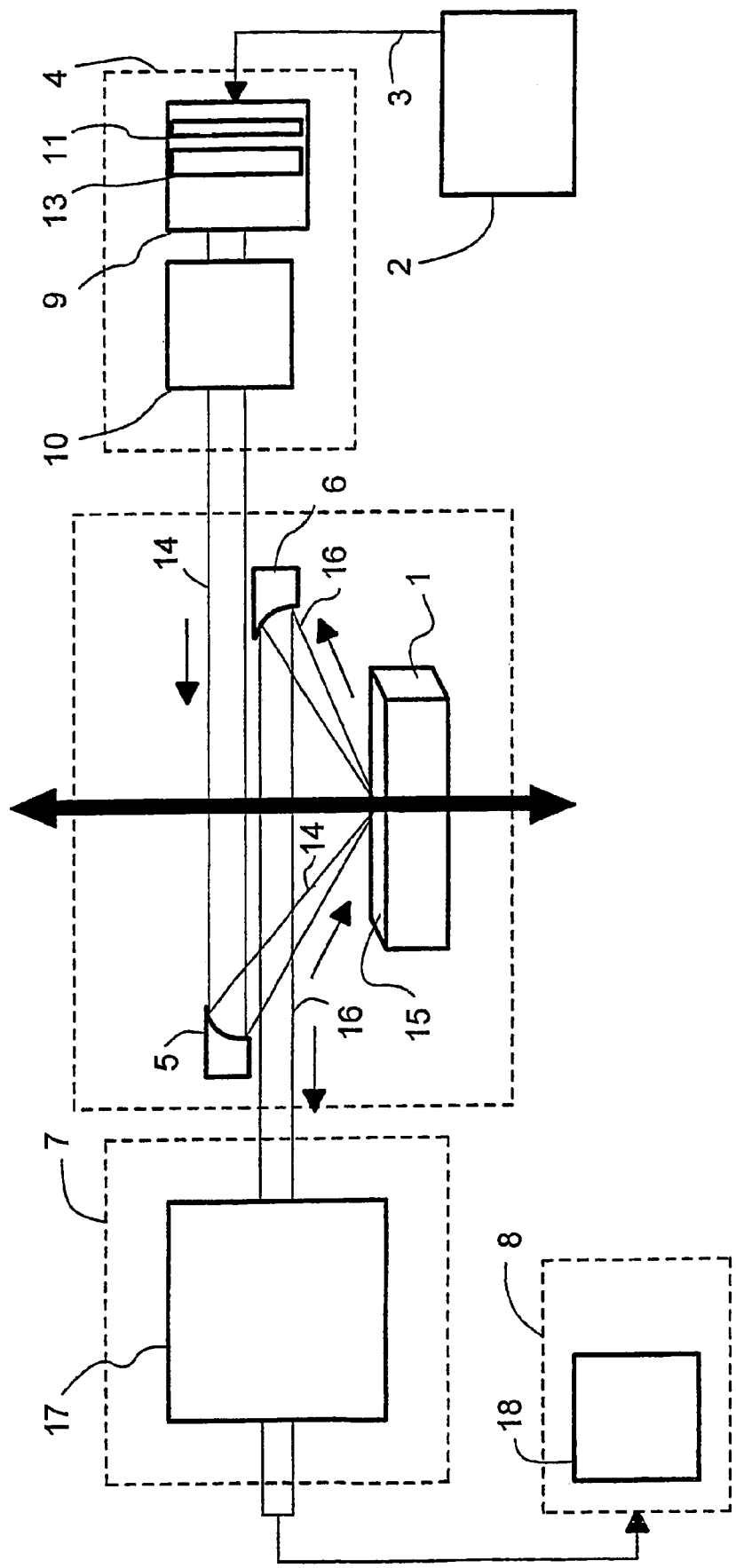
FIG. 5 shows the relative movement of both parabolic mirrors and the sample with respect to the polarisation state generator section and analysing section to vary the incidence angle θ.

FIG. 5 shows a second embodiment, in which both mirrors 5, 6 and the sample 1 are vertically translated with respect to the analysing section 7 and the polarisation state generator section 4 to vary the incidence angle θ.

Advantageously, the incidence angle θ can be largely varied, i.e. said angle can take any value between 0° and 90°.

The specifications of the ellipsometric system according to the invention are provided for illustrative purposes only and should not be used to unduly limit the scope of the present invention. For example, the spectroscopic ellipsometer is not limited to measurements performed in reflection, i.e. the change of the polarisation state of the beam occurs upon reflection of said beam on a sample surface but can be adapted for transmission measurements. In the latter case, both parabolic mirrors 5, 6 have in a preferred embodiment common respective axis merged with the sample surface and are symmetrically positioned with respect to the focus of the parabolic mirror. The state of polarisation of the beam changes continuously as light progresses through a medium. [Azzam and Bashara, in "Ellipsometry and polarized light", North-Holland, Amsterdam, 1977].

The invention claimed is:

1. Spectroscopic ellipsometer comprising:
    a light source emitting a light beam,
    a polarization state generator section containing a collimation optic collimating, said and a generator of polarization that polarizes the light beam,
    a first mirror focusing the beam to a small spot on the surface of a sample to an incidence angle θ,
    a second mirror connecting the beam modified by the sample to an analyzing section comprising a polarization analyzer that analyses the beam,
    means for detecting and analyzing spectroscopically said beam,
    wherein
    the first and second mirrors are parabolic mirrors,
    the light beam through the polarization state generator section up to the first mirror is parallel enabling achromatism, and
    said incidence angle θ is largely varied without shifting of the location of the small spot on the sample surface.

2. Spectroscopic ellipsometer according to claim 1, wherein the generator of polarization is a photoelastic modulator.

3. Spectroscopic ellipsometer according to claim 1, wherein the generator of polarization is a rotating analyzer.

4. Spectroscopic ellipsometer according to claim 1, wherein the generator of polarization is a rotating polarizer.

5. Spectroscopic ellipsometer according to claim 1, wherein the generator of polarization is a rotating compensator.

6. Spectroscopic ellipsometer according to claim 1, wherein the polarization state generator section and the analyzing section are translated vertically with respect to the parabolic mirrors to vary the incidence angle θ.

7. Spectroscopic ellipsometer according to claim 6, wherein the incidence θ is varied between 0° and 90°.

8. Spectroscopic ellipsometer according to claim 1, where both mirrors and the sample are vertically translated with respect to the analyzing section and polarization state generator section to vary the incidence angle θ.

9. Spectroscopic ellipsometer accordingly to claim 1 wherein the said two parabolic mirrors have the same optical characteristics.

10. Spectroscopic ellipsometer according to claim 1, where in the axis of both parabolic mirrors and the sample surface are merged.

11. Spectroscopic ellipsometer according to claim 10 wherein both parabolic are positioned symmetrically with respect to a plan passing by their optical axis and being normal to the sample surface.

12. Spectroscopic ellipsometer according to claim 1, wherein the shape of the parabolic mirrors is manufactured by diamond turning.

13. Ellipsometric system according to claim 12, where in the distance from the polarization state generator section to the sample and the distance from the analyzing section to the sample are optimized to avoid diffraction influence created by diamond turning artifact.

14. Spectroscopic ellipsometer according to claim 13, wherein the parabolic mirrors are treated with a post-polishing process.

15. Spectroscopic ellipsometer according to claim 1, wherein the size of the spot is close to the diffraction limits.

* * * * *